(12) United States Patent
Deotte et al.

(10) Patent No.: US 11,130,131 B2
(45) Date of Patent: Sep. 28, 2021

(54) LATTICE MICROFLUIDICS

(71) Applicant: Lawrence Livermore National Security, LLC, Livermore, CA (US)

(72) Inventors: Joshua R. Deotte, Livermore, CA (US); Sarah Baker, Dublin, CA (US); Eric Duoss, Danville, CA (US); Jennifer Marie Knipe, Oakland, CA (US); Fang Qian, Santa Cruz, CA (US); Samantha Ruelas, Newberry Springs, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 122 days.

(21) Appl. No.: 16/584,460

(22) Filed: Sep. 26, 2019

(65) Prior Publication Data

US 2021/0094036 A1    Apr. 1, 2021

(51) Int. Cl.
  *B01L 3/00*    (2006.01)
  *C12M 3/06*    (2006.01)

(52) U.S. Cl.
  CPC ... *B01L 3/502746* (2013.01); *B01L 3/502707* (2013.01); *C12M 23/16* (2013.01); *B01L 2300/0874* (2013.01)

(58) Field of Classification Search
  CPC ....... B01L 2300/0874; B01L 2300/161; B01L 2400/0406; B01L 3/502707; B01L 3/50273; B01L 3/502746; C12M 23/16; C12M 25/14; C12M 33/00
  See application file for complete search history.

(56) References Cited

U.S. PATENT DOCUMENTS

| | | | |
|---|---|---|---|
| 2013/0056912 A1 | 3/2013 | O'Neill et al. | |
| 2013/0143060 A1 | 6/2013 | Jacobsen et al. | |
| 2013/0264749 A1 | 10/2013 | Jones et al. | |
| 2016/0282338 A1 | 9/2016 | Miklas et al. | |
| 2019/0145298 A1* | 5/2019 | Abu Al-Rub | B01D 53/34 55/523 |
| 2021/0053056 A1* | 2/2021 | Dudukovic | B01L 3/502707 |

OTHER PUBLICATIONS

International Search Report and Written Opinion for Application No. PCT/US2020/052210 dated Jan. 4, 2021.
J. Berthier, K. A. Brakke, and E. Berthier, "A general condition for spontaneous capillary flow in uniform cross-section microchannels," Microfluid Nanofluid, vol. 16, No. 4, pp. 779-785, Apr. 2014, doi: 10.1007/s10404-013-1270-1.

(Continued)

*Primary Examiner* — Jennifer Wecker
(74) *Attorney, Agent, or Firm* — Harness, Dickey & Pierce, P.L.C.

(57) ABSTRACT

An engineered unit cell is disclosed for flowing a fluid therethrough in three dimensions. The unit cell may have a substrate with a plurality of flow channels around and between struts formed within the substrate. The struts may each be formed with a desired shape and orientation within the substrate to achieve a desired degree of fluid flow through the flow channels, in each of one of three dimensions, through the unit cell.

19 Claims, 3 Drawing Sheets

(56) References Cited

OTHER PUBLICATIONS

R. S. Hale, R. Ranjan, and C. H. Hidrovo, "Capillary flow through rectangular micropillar arrays," International Journal of Heat and Mass Transfer, vol. 75, pp. 710-717, Aug. 2014, doi: 10.1016/j.ijheatmasstransfer.2014.04.016.

S. Das, H. V. Patel, E. Milacic, N. G. Deen, and J. a. M. Kuipers, "Droplet spreading and capillary imbibition in a porous medium: A coupled IB-VOF method based numerical study," Physics of Fluids, vol. 30, No. 1, p. 012112, Jan. 2018, doi: 10.1063/1.5010716.

J. Cai, E. Perfect, C.-L. Cheng, and X. Hu, "Generalized Modeling of Spontaneous Imbibition Based on Hagen-Poiseuille Flow in Tortuous Capillaries with Variably Shaped Apertures," Langmuir, vol. 30, No. 18, pp. 5142-5151, May 2014, doi: 10.1021/la5007204.

T. Gambaryan-Roisman, "Liquids on porous layers: wetting, imbibition and transport processes," Current Opinion in Colloid & Interface Science, vol. 19, No. 4, pp. 320-335, Aug. 2014, doi: 10.1016/j.cocis.2014.09.001.

P. Randive, A. Dalal, and P. P. Mukherjee, "Mesoscopic Modeling of Capillarity-Induced Two-Phase Transport in a Microfluidic Porous Structure," Transp Porous Med, vol. 122, No. 3, pp. 673-691, Apr. 2018, doi: 10.1007/s11242-018-1020-7.

J. Berthier et al., "On the halt of spontaneous capillary flows in diverging open channels," Medical Engineering & Physics, vol. 48, pp. 75-80, Oct. 2017, doi: 10.1016/j.medengphy.2017.05.005.

M. Prakash, D. Quere, and J. W. M. Bush, "Surface Tension Transport of Prey by Feeding Shorebirds: The Capillary Ratchet," Science, vol. 320, No. 5878, pp. 931-934, May 2008, doi: 10.1126/science.1156023.

M. Liu, S. Suo, J. Wu, Y. Gan, D. AH Hanaor, and C. Q. Chen, "Tailoring porous media for controllable capillary flow," Journal of Colloid and Interface Science, vol. 539, pp. 379-387, Mar. 2019, doi: 10.1016/j.jcis.2018.12.068.

* cited by examiner

LATTICE MICROFLUIDICS

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to microfluidics, and more particularly to systems and methods for open microfluidics which implement a partially enclosed microfluidics structure through a three dimensional lattice of unit cells having a parameterized geometry.

BACKGROUND

The statements in this section merely provide background information related to the present disclosure and may not constitute prior art.

Open-channel microfluidics is a branch of microfluidics that studies devices based on capillary-driven flow with at least one open interface. Since the working fluid is directly accessible and passively driven, open microfluidic devices are used in medical environments for point-of-care sample loading, chemical sensing, and low-cost fluid handling. However, significant limitations exist with present day open microfluidics devices. One significant limitation is that present day open microfluidic devices are typically constrained to enabling flow in two dimensions. Typically, previously developed open microfluidics devices have involved the use of a linear flow channel which consists of a gap between two solid walls, where only two opposing ends or areas (e.g., top and bottom) of the flow channel are open. This permits flow generally in one plane and one direction only, for example along a Z plane or Z direction, but not along an X or Y directions perpendicular to the Z direction. The flow in the other directions (e.g., Y and Z directions in this example) is not possible because the flow channel is typically constrained by the two solid walls.

A microfluidic structure which enables flow to move or propagate along two or more non-parallel paths, for example along perpendicular X, Y and Z axes, would enable dramatically greater possibilities for a number of applications including bioreactors/chemical sensing and biocatalysis.

SUMMARY

This section provides a general summary of the disclosure, and is not a comprehensive disclosure of its full scope or all of its features.

In one aspect the present disclosure relates to an engineered unit cell for flowing a fluid therethrough in three dimensions. The unit cell may comprise a substrate, and a plurality of flow channels formed between and around a plurality of struts. The struts are within the substrate. The struts may each be formed with a desired shape and orientation within the substrate such that the flow channels achieve a desired degree of fluid flow in each of three dimensions, through the unit cell.

In another aspect the present disclosure relates to an engineered, open channel, multi-cell structure for flowing a fluid therethrough in three dimensions. The structure may comprise a plurality of unit cells formed adjacent to one another. The unit cells may have a shape enabling the unit cells to be tessellated to form a three dimensional configuration of contiguous ones of the unit cells. Each of the unit cells may have at least one flow channel between or around a strut, where the strut extends through the unit cell, and connects with a strut of at least one other one of the unit cells. The struts each may be formed with a desired shape and orientation within the substrate to achieve a desired degree of fluid flow in each of three dimensions, through the structure.

In still another aspect the present disclosure relates to a method for forming an open wall, engineered structure for flowing a fluid therethrough in three dimensions, in a controlled manner. The method may comprise forming a plurality of unit cells in an engineered, contiguous pattern using a material. The unit cells may further be formed with a shape enabling the unit cells to be tessellated to form the engineered structure with substantially no gaps or voids between adjacent ones of the unit cells. The method may further include forming the plurality of unit cells with a plurality of flow channels around or between a plurality of struts, and where the struts extend through the material. The method may further involve forming each of the struts to extend fully through the unit cell.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure. Corresponding reference numerals indicate corresponding parts throughout the several views of the drawings. In the drawings.

DETAILED DESCRIPTION

Figure 1:
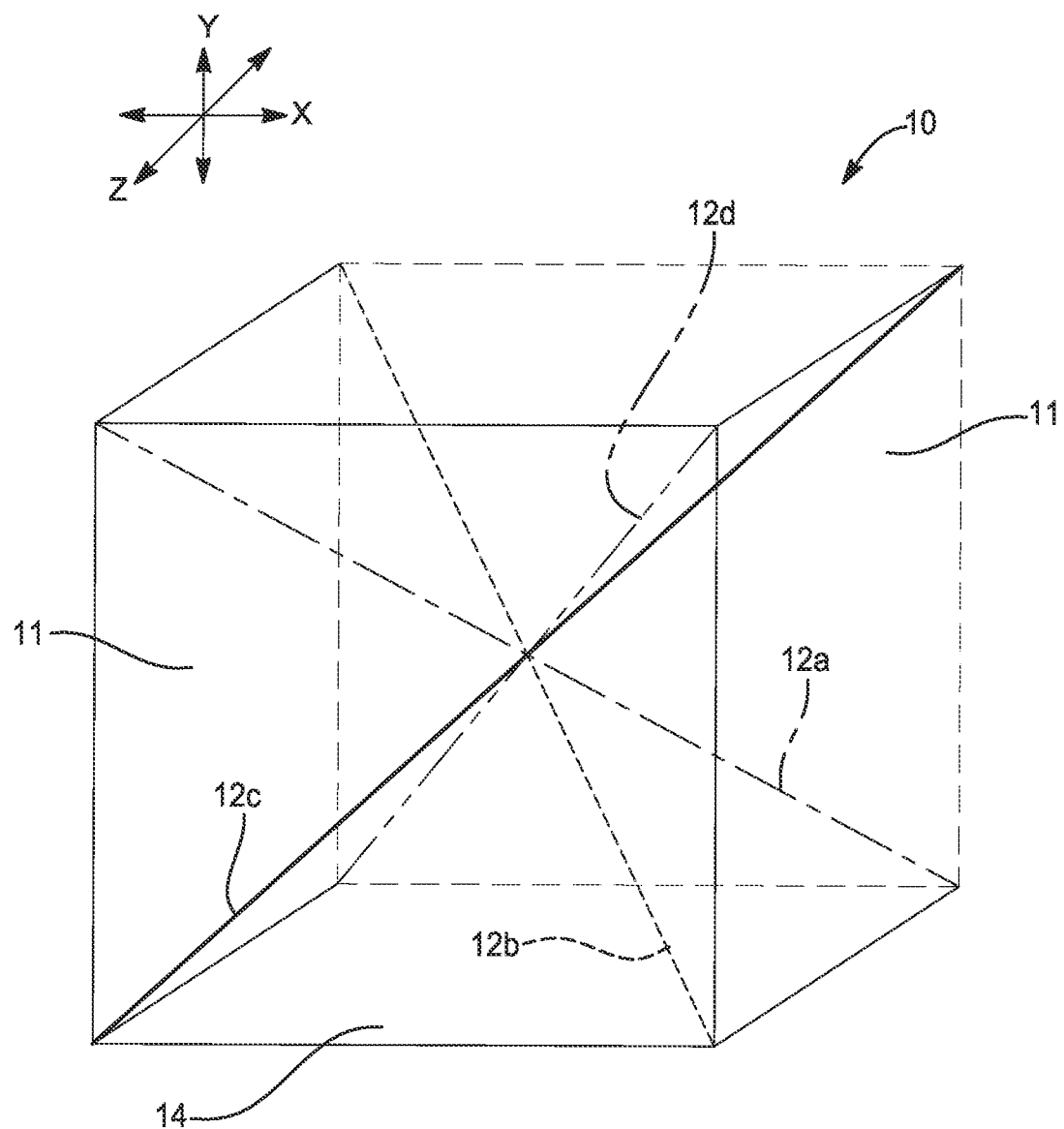
FIG. 1 is an isometric view of an engineered unit cell in accordance with one embodiment of the present disclosure.

Example embodiments will now be described more fully with reference to the accompanying drawings. The present invention relates to a microfluidics system and method which enables full, three-dimensional control and parametrized flow throughout a domain of a structure. The various embodiments of the present disclosure also increase surface area contact between phases per unit volume of fluid, since all sides of a structure made in accordance with the present disclosure can be open. Referring to FIG. 1, an engineered, single lattice unit cell 10 is shown in accordance with one embodiment of the present disclosure. The use of the term "engineered", as used throughout the following discussion, is intended to denote that the features of the unit cell 10 are not randomly formed, but rather carefully predetermined and manufactured with a specific application/performance and/or specific flow requirements in mind.

In this example the unit cell 10 includes a plurality of voids which form distinct fluid flow paths or flow channels 11 within the unit cell 10, in between and around structural elements 12a-12d. For convenience, the structural elements 12a-12d will be referred to throughout the following discussion as "struts" 12a-12d. The flow channels 11 can be thought of as being somewhat similar to a network of blood vessels in a human body, in that they form a branch network of fine fluid channels which extend around the struts 12a-12d and through a substrate 14 of the unit cell 10. In this example the unit cell 10 comprises a cube-shaped unit cell, and each one of the four struts 12a-12d span between two opposing corner points of the unit cell such that all eight corners of the unit cell 10 are connected to at least one of the struts 12a-12d. In the example unit cell 10 shown in FIG. 1, this arrangement of the struts 12a-12d provides an intersection point at the geometric center of the unit cell 10 where all of the struts intersect.

The substrate 14 may be comprised of any number of different materials, which will largely depend on the specific application for which the unit cell 10 is being used. In some embodiments the substrate 14 may be made from one or more of metal, plastic, or even ceramic, or possibly even a mixture of two or more materials, where one material is used to form a portion of the unit cell 10 (or multiple cells 10), while a different material is used to form a different portion of the same unit cell 10 (or to form different unit cells 10). Preferably, the material selected will be adaptable for use in an additive manufacturing (AM) process, for example stereolithography, direct-ink-write, or electrophoretic deposition. Still further, the material chosen for the substrate 14 is preferably "functionalized" to interact with the fluid being used with the unit cell 10 so that capillary flow can be established, which can involve chemical or mechanical modification of the surface. Modification can occur through various pathways such as O2 plasma etching, chemical etching, abrasion, and polymerization of functional groups to the surface. Texturing a surface tends to enhance its effect on water. Hydrophilic becomes more hydrophilic with micro-patterning or nano-patterning, and the same applies for hydrophobic. Combining chemical modification and topological modification in many instances yields the best result. In the example of FIG. 1, the unit cell 10 is a square shaped cell and the struts 12a-12d are perfectly linear, consistent cross-sectional thickness struts (i.e., all have the same diameter). Again, this is just one example, and the struts 12a-12d need not be of the same diameter, but instead they may have different diameters, or even changing diameters throughout each of their lengths. Furthermore, they need not be perfectly linear struts 12a-12d, but instead may include one or more curving, wavy, zig zag, etc. shapes. Furthermore, the struts 12a-12d may be intermixed to have different shapes, for example one or more straight struts may be intermixed in a given unit cell 10 with one or more curving struts, and struts of one diameter may be intermixed with struts having one or more differing diameters.

The struts 12a-12d need not be engineered to have a constant cross-sectional shape or dimension, but could assume different cross sectional shapes throughout their lengths, and/or have different cross-sectional dimensions over their lengths. Still further, the struts 12a-12d need not be configured to insect at the geometric center, but instead may intersect at a different location (i.e., at a non-geometric center point) of the unit cell 10. Still further, the struts 12a-12d may intersect at one (or even two or more) different (non-geometric center) points within the unit cell 10, or there may be no intersection between any two of the struts 12a-12d. By changing various parameters such as the diameter/shape/cross-sectional area of the struts 12a-12d, and/or the overall number of struts within the unit cell 10, and/or their orientations within the substrate 14, the capillary-driven flow through the flow channels 11 of the unit cell 10 can be controlled in one, two or three axes (i.e., along one, two or three of the X, Y and Z axes).

And while the unit cell 10 is shown as a square shaped cell, any other shape that can be tessellated can be used. For example, the unit cell 10 may be formed by three dimensional structures such as cuboids, octahedrons, icosahedrons, hexagonal pyramids, square pyramids, prisms, pyramids, pentagons, hexagons, octagons, dodecahedrons, etc., just to name a few possible cell shapes. However, it is expected that tetrahedra and hexahedra structures are likely to be especially popular and useful, because there are many tools (i.e., used for meshing finite element simulations) that handle the types of mesh generation related to tetrahedra and hexahedra structures.

Figure 2:
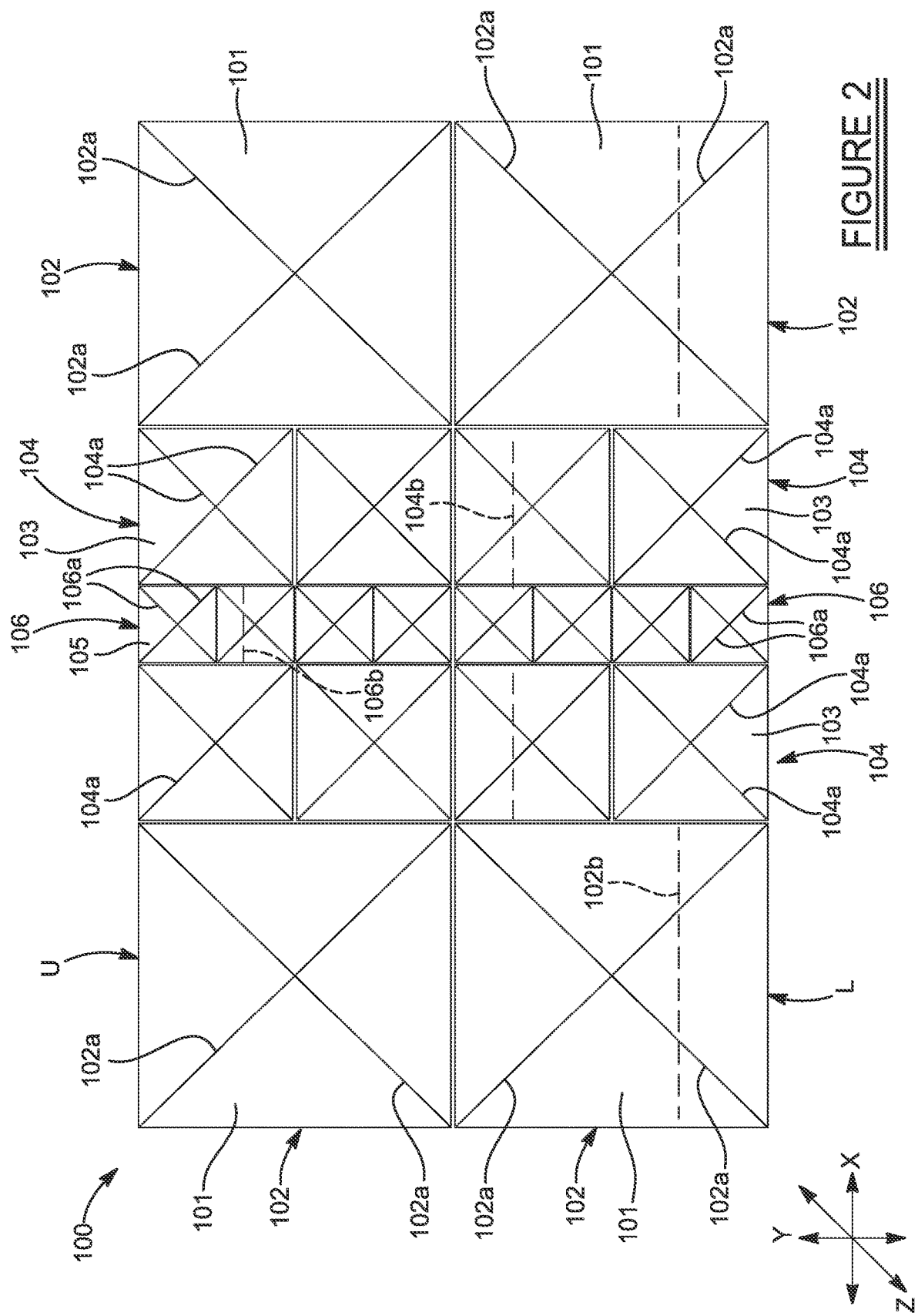
FIG. 2 is a front view of an engineered unit structure comprised of different unit cells.

FIG. 2 shows a two-dimensional illustration of a three-dimensional, engineered, multi-cell structure 100, which forms a flow cell in accordance with another embodiment of the present disclosure. In this example the structure 100 forms a lattice of interconnected, three-dimensional unit cells 102, 104 and 106, which are of three differing sizes, and interconnected with adjacent unit cells at multiple points. While the illustration of FIG. 2 is a two-dimensional illustration, it will be appreciated that each of the unit cells 102, 104 and 106 includes a construction like that shown for unit cell 10 in FIG. 3, and therefore each unit cell 102/104/106 is able to produce a fluid flow in three dimensions.

The structure 100 of FIG. 2 makes use of a plurality of tessellated unit cells 102, 104 and 106, where all of the cells are formed, in this example, as cubic square unit cells. The structure 100 thus forms a contiguous domain extending in three dimensions. Flow channels 101 are defined around and between the struts 102a, where the struts 102a are formed within unit cells 102, and flow channels 103 are formed around and between struts 104a, where the struts 104a are formed within unit cells 104, where the struts 104a are smaller in diameter than the struts 102a. Flow channels 105 are formed around and between struts 106a, where the struts 106a are formed within unit cells 106, and the struts 106a are smaller in diameter than the struts 104a. The struts 102a/104a/106a of each one of the unit cells 102/104/106 are in flow communication with at least one strut of a different unit cell, and more preferably with two or more struts of a different/contiguous unit cell. Again, while the struts 102a/104a/106a are shown as linear struts, they need not necessarily be linear, but rather could be curving or could assume other shapes. The struts 102a/104a/106a communicate with the eight corners of their respective unit cell 102/104/106.

Just as one example, the diameter of the struts 102a may be significantly larger, for example on the order of $1\times10^1$ or $1\times10^2$ larger than the diameter of the struts 104a, and the diameter of the struts 104a may be $1\times10^1$ or $1\times10^2$ larger than struts 106a. In this example, the capillary force of unit cells 106, 104, and 102 can be balanced by increasing the diameter of the struts while also increasing the overall size of the unit cell. Since the capillary pressure is directly related to contact line of the struts and the fluid and inversely proportional to the cross-sectional area of the fluid surface creating those contact lines, larger struts can counteract the increase in unit cell size. Consequently, the capillary pressure of unit cell 102 can be matched closely to the capillary pressure in 106 even though their sizes are substantially different, resulting in capillary flow originating at "L" and reaching the top "U" of the structure. Without adjusting the strut diameters, fluid would completely fill the stack of unit cells 106 but 104 and 102 would only partially fill.

From the structure 100 of FIG. 2, one can understand that the structure 100 can be engineered to control the capillary flow through the flow channels 101, 103 and 105 of the structure along one, two, three or more non-parallel planes, based on the construction of the unit cells 102/104/106 used. To create paths with a stronger capillary flow, more cells 106 would be used to create such paths. To create more paths of lesser capillary flow, more of the unit cells 102 or 104 would be used to create such paths. Alternatively, the diameters of the struts can be varied while keeping the unit cell size constant or even a different distribution of struts within the cell. A combination of these methods can be used to amplify the effect of each change. The unit cells 102/104/106, because of the different engineered constructions of the struts 102a/104a/106a, create different degrees of capillary flow action for a fluid, for example water, which causes the water to flow spontaneously through the entire structure 100 when the water enters the struts 102a/104a/106a at the lowermost end L of the structure 100, with different portions of the structure 100 producing a much greater volume of water flow through the structure than other portions. Still further, the structure 100 may be constructed with larger, internal hollow areas, or internal portions with denser concentrations of struts 102a/104a/106a, to further influence the flow of fluid through the structure 100.

The selection of different unit cell constructions can achieve different levels of equilibrium within the structure. For example, with the unit cells 102, 104 and 106 shown in FIG. 2, dashed line 106b represents an equilibrium level that fluid being drawn into the unit cells 106 by capillary action may reach. Dashed line 104b represents an equilibrium level for the fluid drawn into the unit cells 104, and the dashed line 102b represents the equilibrium level for the fluid drawn into the unit cells 102. The significantly weaker capillary action within the unit cells 104 and 102 result in significantly lower levels of fluid equilibrium within the structure 100. It will be appreciated, then, that selective placement and/or concentrations of unit cells 102/104/106 within the structure 100 can create dramatically different capillary flows through the structure.

To provide further control over the flows through the structure 100, the head pressure of the water (or other fluid being used) may be increased in one or more of the unit cells 102, 104 and/or 106. For example, increasing pressure can also be used to dynamically change the flow path into adjacent unit cells. After unit cells 106 have been preferentially filled by capillary-driven flow, pressure can be applied, which will result in the fluid flowing into the next row of unit cells 104. Once filled, unit cells 106 and 104 will entrap fluid, which can be driven by a small inlet pressure.

Figure 3:
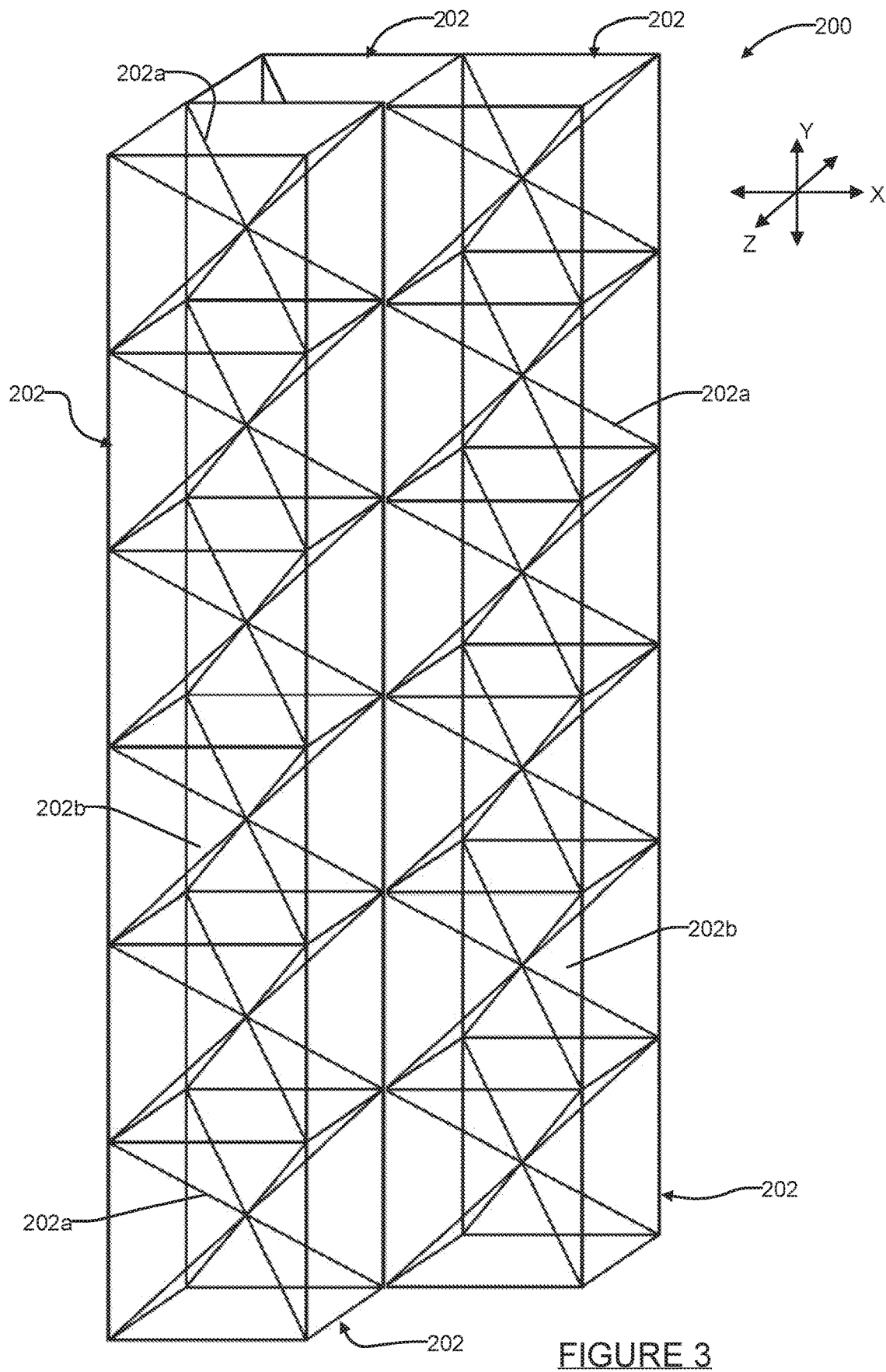
FIG. 3 is an isometric view of an engineered unit structure in accordance with another embodiment of the present disclosure, where the engineered unit structure is comprised of three contiguous columns of unit cells, and wherein the unit cells have a common dimension and construction.

FIG. 3 shows a structure 200 made up of a three-dimensional lattice of unit cells 202 formed by square shaped unit cells 202 having a plurality flow channels 202b around and between struts 202a and arranged in three contiguous columns. The structure 200 will provide fluid propagation paths through capillary action along planes extending in each of the X, Y and Z axes.

The various embodiments discussed herein enable the flow characteristics of the structures 10, 100 and 200 to be changed throughout the domain. By increasing at least one of the voids (e.g., reducing diameters of the struts) or the size of unit cells (e.g., unit cells 102 or 104 or 106), spontaneous capillary flow can be reduced. Alternatively, by increasing the density of the unit cell, pressurized flow can be inhibited. In this case, making the structures denser (solid) will produce high capillary force but if driven by pressure, will provide increasing hydraulic resistance.

With a parameterized geometry such as described and illustrated herein, the effective flow properties of each of the structures 10, 100 and 200 can be changed discretely throughout the domain if desired. And while the use of a three-dimensional printer is expected to be a popular means for manufacturing the structures 10, 100 and 200, a more limited geometry subset could be fabricated by other manufacturing means. Preferably, the substrate material's surface is modified to preferentially interact with the fluid being used so that capillary flow can be established. By "modified", it is meant that hydrophilic polymers are reacted onto the surface to make it more hydrophilic. Alternatively, one may use oxygen-plasma treatment to increase surface energy and make the structures hydrophilic. Fundamentally, in regard to flow of water within the structure, one is dealing with surface energy and contact angle. Thus, it will be appreciated that surface functionality (or hydrophilicity) can also have a profound impact if it is spatially patterned.

The various embodiments discussed herein form open microfluidic devices which are expected to be particularly useful in medical environments for point-of-care sample loading, in chemical sensing, and also low-cost fluid handling applications. The ability to change the geometry and size of each unit cell, to control/manage flow properties in three dimensions, is also expected to find significant utility in bio-patterning for 3D bioreactors and cell cultures. Directly patterning live cell cultures into 3D constructs is challenging due to the largely incompatible requirements of cell growth and 3D printing. Instead, a hydrophilic 3D structure can be printed with conventional 3D printing methods and modified to become hydrophilic. After modification and sterilization, the structure can be infilled with a cell-laden gel. This allows a decoupling of the 3D printing chemical requirements and the biological requirements. As another example, in bioreactors/chemical sensing, reactions can involve immiscible species, proceeding only at the phase-separation interface. Biocatalysis of methane to methanol is one example. By increasing the interfacial surface area, lattice microfluidics can improve the per-unit efficiency of chemical sensing platforms.

The various embodiments described herein can each be used alone, relying on capillary action to transport fluid, or each can be used with a pump. In a pumping configuration, the flow profile through the structure 10, 100 or 200 changes so that both surface tension and the unit cell geometry constrain the flow pattern through the domain. As noted above, altering the head pressure will also enable the flow domain to be adjusted, but still affected at least partially by the unit cell parameters.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An engineered unit cell for flowing a fluid therethrough in three dimensions, the unit cell comprising:
   a substrate;
   a plurality of flow channels formed between and around a plurality of struts, the struts being disposed within the substrate; and
   the struts each formed with a desired shape and orientation within the substrate such that the flow channels are configured to achieve a desired degree of fluid flow in each of three dimensions, through the unit cell; and
   wherein the unit cell forms a shape that can be tessellated so as to be configured with additional cells of the same shape into a contiguous structure.

2. The unit cell of claim 1, wherein the struts comprise linear struts.

3. The unit cell of claim 1, wherein the struts are dimensioned to cause the flow channels to create a capillary flow action when a fluid is exposed to at least one of the flow channels.

4. The unit cell of claim 1, wherein the struts all intersect within the substrate.

5. The unit cell of claim 1, wherein the struts extend non-parallel to one another.

6. An engineered, open channel, multi-cell structure for flowing a fluid therethrough in three dimensions, the structure comprising:
   a plurality of unit cells formed adjacent to one another;
   the unit cells having a shape enabling the unit cells to be tessellated to form a three-dimensional configuration of contiguous ones of the unit cells;
   each of the unit cells having flow channels around at least one strut, wherein the strut extends through the unit cell, and the strut being in communication with a strut of at least one other one of the unit cells; and
   the struts each formed with a desired shape and orientation within the structure such that the struts are configured to cause the flow channels achieve a desired degree of fluid flow in each of three dimensions, through the structure.

7. The structure of claim 6, wherein each of the unit cells include a plurality of struts.

8. The structure of claim 7, wherein the plurality of struts of a given one of the unit cells intersect at least at one point within the given one of the unit cells.

9. The structure of claim 6, wherein the plurality of struts form a plurality of linear struts.

10. The structure of claim 7, wherein the plurality of struts of different ones of the unit cells have different cross-sectional dimensions.

11. The structure of claim 7, wherein the unit cells each comprise square shaped unit cells, and wherein each said unit cell comprises a plurality of four struts, each one of the four struts spanning between two corner points of the unit cell.

12. The structure of claim 11, wherein the plurality of four struts intersect at a geometric center of the unit cell.

13. A method for forming an open wall, engineered structure for flowing a fluid therethrough in three dimensions, in a controlled manner, the method comprising:
   forming a plurality of unit cells in an engineered, contiguous pattern using a material, the unit cells further being formed with a shape enabling the unit cells to be tessellated to form the engineered structure with substantially no gaps or voids between adjacent ones of the unit cells;
further forming the plurality of unit cells with a plurality of struts extending through the material, wherein areas around and between the struts form flow channels within the material; and
further forming each of the struts to extend fully through the unit cell.

14. The method of claim 13, wherein further forming the plurality of unit cells with a plurality of struts comprises forming each of the unit cells with a plurality of linear struts.

15. The method of claim 14, further comprising forming each of the linear struts such that the linear struts within a given one of the unit cells extend non-parallel to one another.

16. The method of claim 13, further comprising forming the unit cells as cubic square shaped unit cells.

17. The method of claim 16, further comprising forming each of the struts as linear struts.

18. The method of claim 17, further comprising forming each one of the plurality of struts such that each communicates with two opposing corners of its associated said square shaped unit cell.

19. The method of claim 13, further comprising forming the plurality of struts such that the plurality of struts all intersect one another at a geometric center of their associated said unit cell.

* * * * *